(12) United States Patent
Burnett et al.

(10) Patent No.: US 8,535,265 B2
(45) Date of Patent: Sep. 17, 2013

(54) TRACHEAL CATHETER WITH SUCTION LUMEN PORT IN CLOSE PROXIMITY TO THE CUFF

(75) Inventors: Steven Ray Burnett, Woodstock, GA (US); Stephen A. Baratian, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 469 days.

(21) Appl. No.: 12/644,111

(22) Filed: Dec. 22, 2009

(65) Prior Publication Data

US 2011/0146691 A1 Jun. 23, 2011

(51) Int. Cl.
*A61M 29/00* (2006.01)
*A61M 16/00* (2006.01)

(52) U.S. Cl.
USPC .................. 604/102.01; 606/196; 128/207.15

(58) Field of Classification Search
USPC .................... 604/94.01, 95.03, 96.01, 102.01, 604/102.03, 103, 908, 912, 915; 128/207.15; 606/192, 194, 196–198
See application file for complete search history.

(56) References Cited

U.S. PATENT DOCUMENTS

| | | | |
|---|---|---|---|
| 4,305,392 A * | 12/1981 | Chester | 604/98.01 |
| 4,584,998 A | 4/1986 | McGrail | |
| 4,840,173 A | 6/1989 | Porter, III | |
| 5,201,310 A | 4/1993 | Turnbull | |
| 5,311,864 A | 5/1994 | Huerta | |
| 5,520,175 A | 5/1996 | Fry | |
| 6,802,317 B2 | 10/2004 | Göbel | |
| 7,293,561 B2 | 11/2007 | Madsen et al. | |
| 7,581,541 B2 | 9/2009 | Madsen et al. | |
| 2001/0054425 A1 * | 12/2001 | Bertram | 128/207.15 |
| 2007/0089748 A1 | 4/2007 | Madsen et al. | |
| 2008/0021386 A1 * | 1/2008 | Clayton | 604/104 |
| 2008/0047562 A1 * | 2/2008 | Colburn et al. | 128/207.14 |
| 2008/0053454 A1 * | 3/2008 | Pasillas et al. | 128/207.15 |
| 2008/0110468 A1 * | 5/2008 | Nelson et al. | 128/207.15 |
| 2008/0121236 A1 | 5/2008 | Field | |
| 2008/0163870 A1 | 7/2008 | Kusunoki et al. | |
| 2008/0207996 A1 | 8/2008 | Tsai | |
| 2009/0025729 A1 | 1/2009 | Nomori | |
| 2009/0101152 A1 | 4/2009 | Burk et al. | |
| 2009/0287050 A1 * | 11/2009 | Barthel | 600/115 |
| 2010/0186749 A1 * | 7/2010 | Macan et al. | 128/207.15 |

FOREIGN PATENT DOCUMENTS

WO WO 2008/060497 A2 5/2008

* cited by examiner

*Primary Examiner* — Quynh-Nhu H Vu
(74) *Attorney, Agent, or Firm* — James B. Robinson

(57) ABSTRACT

Endotracheal and tracheostomy tubes have an inflatable cuff for sealing the trachea so that a patient may be ventilated through a respiratory lumen of the tube. As a result of sealing the trachea outside of the tube, liquids accumulate above the cuff. If these liquids are allowed to move into the lungs, they may cause ventilator acquired pneumonia (VAP). The liquids may be removed by suction applied to a suction lumen terminating in a port above the cuff, but suctioning can cause damage to the trachea if the tube is sucked up against the tracheal wall. A tracheal catheter having a unique method of attaching the balloon cuff is provided. The cuff is to attached so that an upper part (collar) of the cuff is used to cover the distal end of a suction lumen port. This allows the port to be located closer to the cuff and so provides more thorough liquid removal and reduces the possibility that the tube may suck itself onto the tracheal wall.

4 Claims, 3 Drawing Sheets

TRACHEAL CATHETER WITH SUCTION LUMEN PORT IN CLOSE PROXIMITY TO THE CUFF

The present disclosure relates to a tracheal catheter or tube used for mechanical ventilation of a hospital patient, by insertion of the tube into the trachea of the patient. In particular, the present disclosure relates to a tracheal tube having means for irrigating and/or evacuating contaminated secretions accumulating above the tracheal tube cuff and thereby reducing the risk of such contaminated secretions entering the lungs of the patient.

There are two principle types of tracheal catheters or tubes; the endotracheal tube (ET tube) and the tracheostomy tube (trach tube). The ET tube is inserted through the mouth of a patient and guided past the vocal cords and glottis into the trachea. The trach tube is inserted directly into the trachea through a stoma created in the throat and the tracheal wall by surgical means and enters the trachea below is the glottis. Both types of tube have a relatively large main ventilating lumen that delivers the air from a mechanical ventilating device to the lungs. Both types of tubes typically terminate at a position above the carina, anterior to a position between the second and fourth thoracic vertebrate. Gases may then be introduced through the tracheal tube and into the lungs of the patient.

The primary purposes of tracheal intubation, are to mechanically ventilate the patient's lungs, when a disease prevents the patient from normal, breathing induced ventilation, or to apply anesthetic gases during surgical intervention. In order to create enough air pressure to accomplish such mechanical ventilation and to prevent escape of gases past the tube, it is necessary to seal the passageway around the tracheal tube. A seal may be produced by the use of an inflatable cuff or balloon formed integrally with and surrounding the tracheal tube. When the tracheal tube has been introduced into the patient's trachea, the inflatable cuff will normally be located about 3 to 5 centimeters above the carina and within the tube-like trachea.

The inflatable cuff is then inflated so as to engage the wall of the trachea and thereby seal the trachea and prevent gases being introduced through the tracheal tube from simply turning back up around the tube and passing out of the patients mouth and nose. While treatment of this sort has proved successful for patients having chronic or acute respiratory diseases, there is a constant risk of several complications.

In particular, many patients receiving tracheal intubation develop pneumonia, resulting from an infection of the lungs, possibly induced by contaminated, pooled secretions entering the trachea and the lungs after bypassing the inflatable cuff during intubation. This problem, ventilator acquired pneumonia or VAP, occurs with ET and trach tubes. It is more frequent in the case of ET tubes since when an ET tube is in place the epiglottis, which normally operates as a valve that selectively closes the entry into the trachea and lungs to prevent the introduction of secretions and particulate matter, is held in an open position and secretions which would normally be directed away from the trachea and into the digestive system, instead follow the path of the ET tube and pool above the inflatable cuff of the tracheal tube.

There is a risk of the infectious secretions reaching the lungs during the intubation, by aspiration of the secretions that are able to get past the tracheal tube cuff. However, the greatest risk of such infectious secretions reaching the lungs is upon the cessation of mechanical ventilation. In particular, when the need for tracheal intubation ends, the inflatable cuff of the tracheal tube is deflated so that the tracheal tube may be withdrawn from the patient. The infectious secretions which have pooled above the inflatable cuff are then released and are free to flow into the lungs, where bronchitis or pneumonia may rapidly develop.

To overcome these risks, it is known in the prior art to combine a single suction tube or lumen with a tracheal tube. The suction lumen is joined to the tracheal tube in a suitable manner, the end of the suction lumen terminating at a port in a position above the inflatable cuff. The suction lumen provides means for suction or evacuation of any pooled secretions which accumulate in the trachea above the inflatable cuff. Such prior art devices have the disadvantage that the suction lumen must terminate some distance above the upper or proximal shoulder of the cuff in order to allow for the attachment of the cuff to the tracheal tube body. This distance allows some volume of secretions to be, in effect, unreachable by the suction lumen. In addition, since the suction lumen port is spaced a distance from the cuff, such prior art tubes can allow the suction lumen port to adhere to the tracheal wall during suctioning, causing trauma to the tracheal wall and occluding the suction lumen port.

U.S. Pat. No. 4,840,173 to Porter III, describes an ET tube having a single suction tube merged thereto. In particular, this patent describes a device wherein the suction tube is laminated to the outside of the ventilation tube, so that the suction tube terminates at a position just above the inflatable cuff. The suction tube includes multiple openings which may be used to evacuate secretions which pool above the inflatable cuff. In addition, the inflatable cuff includes a section immediately adjacent to the end of the suction tube that is less flexible than the rest of the inflatable cuff, to ensure that the flexible material of the inflatable cuff is not sucked up against the suction tube openings. The tracheal tube described in the Porter III patent has the disadvantages noted above, that the single lumen suction tube terminates a distance above the upper surface of the cuff, allowing a certain volume of secretions to is remain above the cuff, even after suctioning.

US patent publication 2008/0053454 to Pasillas et al. describes an ET tube wherein the cuff is attached to the tube so that the proximal collar of the cuff is partially inverted, producing a double thickness collar. The publication teaches that this double thickness collar may help reduce or eliminate possible occlusion of the port and may help prevent the port from coming in contact with the tracheal wall.

What is needed is a tracheal catheter capable of suctioning secretions that have pooled above the inflatable cuff, more thoroughly than has been the case so far, with less chance that it will cause trauma to the tracheal wall.

SUMMARY

The present disclosure improves upon a tracheal catheter by attaching the cuff to the tube in a manner that overlays or covers part of the suction port. Part of the collar of the cuff may actually be located partially inside the suction lumen port, without obstructing the part of the suction lumen proximal to the suction lumen port. The proximal collar of the cuff may also block the part of the suction lumen that is distal to the port, instead of merely laying in or on the port.

In one embodiment, the tracheal tube is formed from a flexible cannula having a length, a distal end, and a proximal end. The cannula consists of a plurality of walls extending substantially along the length of the cannula, dividing the cannula into a plurality of separate lumens including a respiratory lumen, a suction lumen, a rinse lumen, and an inflation lumen. An inflatable cuff surrounds the cannula proximal to the distal end. The inflatable cuff is adapted to seal the trachea of a patient. The inflation lumen is in fluid communication with the inflatable cuff. The cuff is attached so that an upper part (collar) of the cuff partially overlays the suction lumen port. This allows the port to be located closer to the cuff and so provides better liquid removal and reduces the possibility that the tube may suck itself onto the tracheal wall.

Other objects, advantages and applications of the present disclosure will be made clear by the following detailed description of a preferred embodiment of the disclosure and the accompanying drawings wherein reference numerals refer to like is or equivalent structures.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. In particular, though most references herein are to an ET tube since the problem of aspirated secretions is greater when using ET tubes, these teachings apply equally to trach tubes. Those skilled in the art will appreciate that aspects of the various embodiments discussed may be interchanged and modified without departing from the scope and spirit of the disclosure.

In manufacturing a tracheal tube, the main cannula is generally extruded by conventional means. As it is extruded in a never ending tube, the cannula is given three lumens; the main respiratory lumen, a cuff inflation lumen, and a suction lumen, separated by internal walls. There may be more lumens extruded into the cannula for additional functions, but the three recited are the lumens of concern for this disclosure. These lumens extruded into the cannula extend the entire length of the cannula. Once the cannula is cut to the proper length, the cuff inflation port and the suction port are located and "skived" or cut out, a technique that is well known to those skilled in the art. This allows liquid communication of each lumen (suction and inflation) through the wall of the cannula to its respective port, opening into the space outside the cannula. The remaining distal portion of the cuff inflation and suction lumens are then blocked below the skived port, generally with a sealing plug. The respiratory lumen extends the entire length of the cannula and is not skived out.

Figure 1:
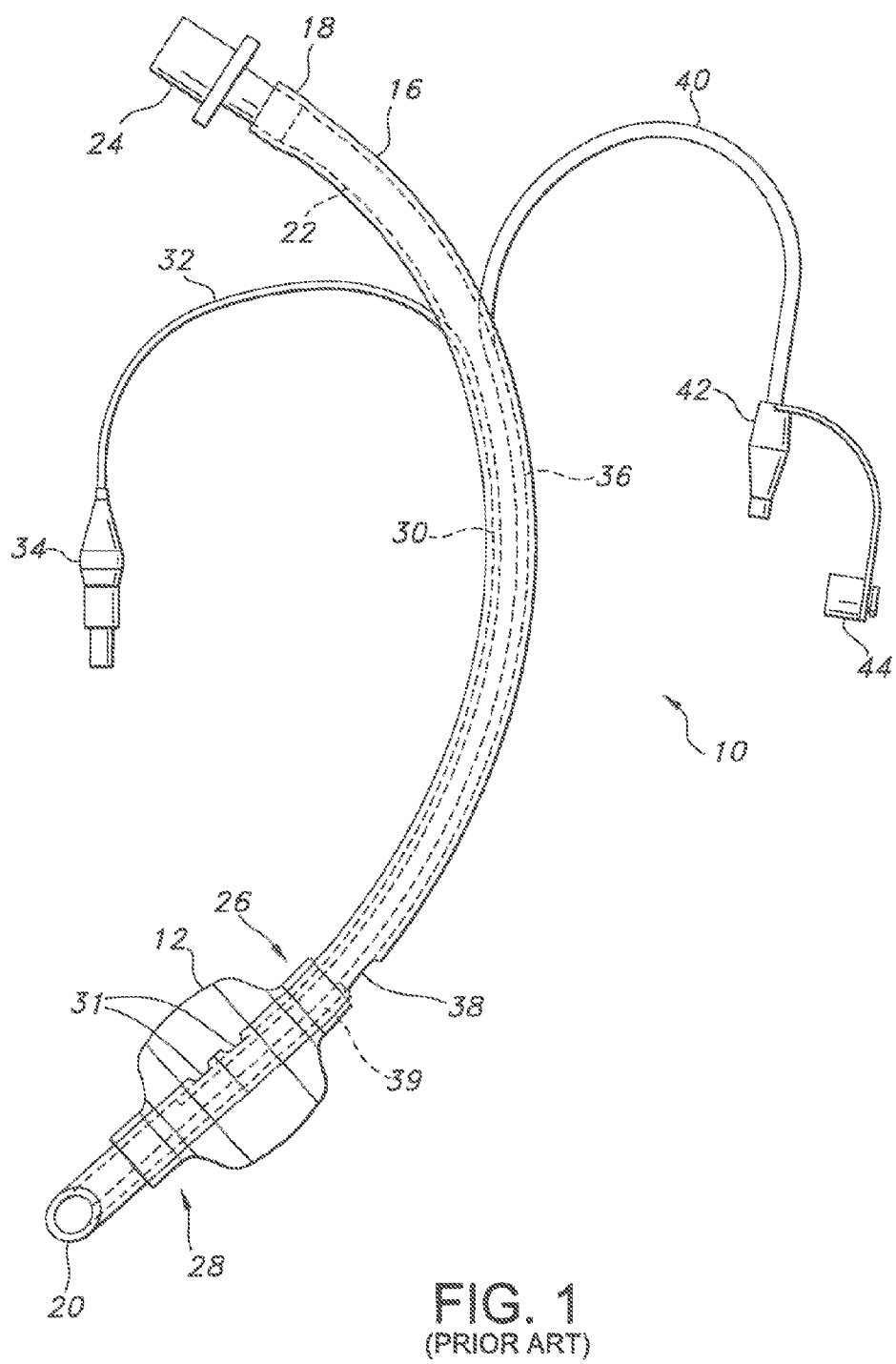
FIG. 1 is a view of an ET tube of the prior art.

Turning to the drawings, FIG. 1 illustrates a prior art ET tube 10 including an inflatable cuff 12. Tube 10 includes a cannula 16 having an open proximal end 18 and an open distal end 20. The cannula 16 defines a gas-conveying lumen 22 for mechanical ventilation of a patient. The proximal end 18 usually includes a connector 24 configured for attachment to a mechanical ventilator (not shown). An inflatable cuff 12 is mounted on the cannula 16 adjacent the distal end 20 of the cannula 16, covering the skived out inflation lumen port(s) 31. The cuff 12 is mounted on the cannula 16 by one or more collars. In FIG. 1, cuff 12 may be mounted on cannula 16 by a first or proximal collar 26 and a second or distal collar 28. During the insertion of the tube 10, the cuff 12 is at least partially collapsed. Once properly in place, the cuff 12 may be inflated via an inflation lumen 30 and cuff inflation port(s) 31 formed in or otherwise associated with the cannula 16. The inflation lumen 30 may be coupled to an inflation line 32 terminating at its proximal end in a fitting 34 that allows inflation of the cuff 12 via the inflation lumen 30 and cuff inflation port(s) 31. The cannula also includes a suction lumen 36 formed in or otherwise associated with the cannula 16. The suction lumen 36 is in liquid communication with a suction lumen port 38 extending through the wall of the cannula 16 through which secretions or other matter accumulated on or proximate the cuff 12 may be removed. The suction lumen 36 extends to the distal end 20 of tubular body 16 and usually includes a sealing plug 39. The suction lumen 36 may be blocked by the sealing plug 39 before the distal end 20 of tubular body 16 or just beyond opening 38. An exterior suction tube 40 is connected to the suction lumen 36 for removing secretions or other matter through the port 38. The suction tube 40 may include an end fixture 42 for attachment to a source of suction (not shown) including a cap 44.

Figure 2:
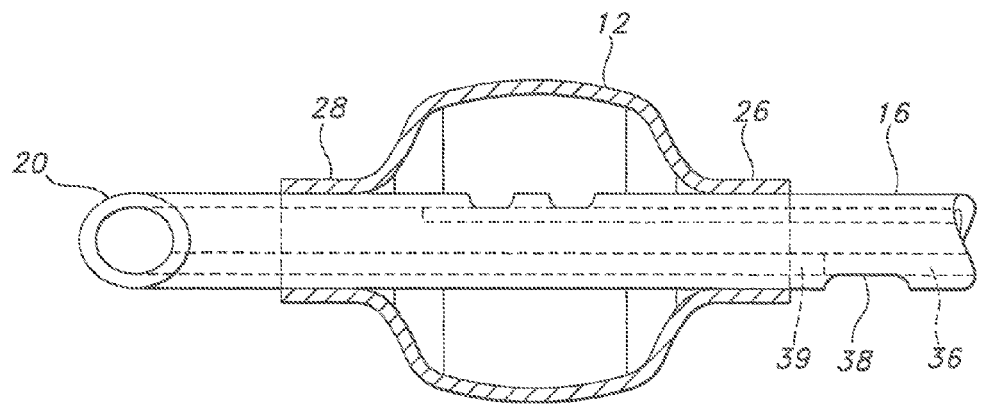
FIG. 2 is a cross-sectional view of the area of attachment of the cuff to the tube of FIG. 1.

Referring to FIG. 2, a cross-sectional view of the cuff 12 and the area of is attachment of the collars 26, 28 to the cannula 16 of FIG. 1 is shown. Both collars 26, 28 are attached around the cannula 16 and sealed and the suction port 38 is spaced some distance from the proximal collar 26. There may be a sealing plug 39 in the suction lumen 36, located distally of the port 38.

Figure 3:
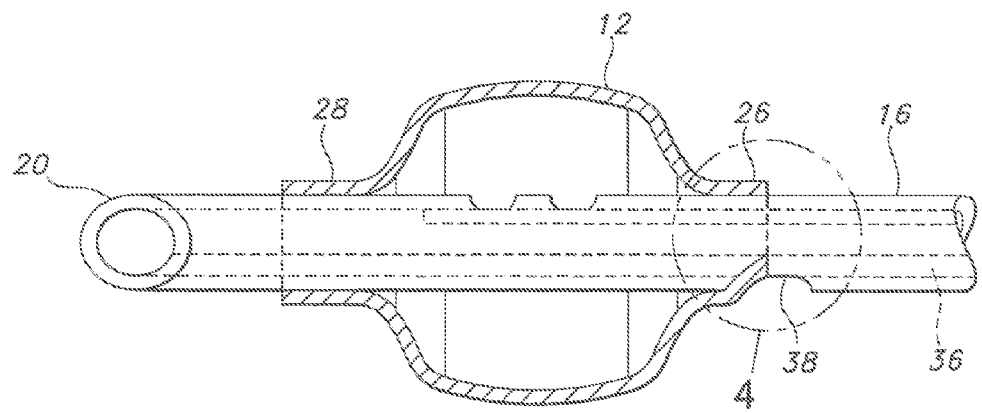
FIG. 3 is a cross-sectional view of the area of attachment of the cuff to the tube of according to this disclosure.

FIG. 3 is a cross-sectional view of the cuff and area of attachment of an embodiment of the disclosed device. In some respects it is similar to the device of FIG. 2, however, the placement of the port 38 and the attachment of the proximal collar 26 are quite different. In this embodiment, a portion of the proximal cuff collar 26 partially covers or overlays the suction lumen port 38. Part of the collar 26 may actually be located partially inside the port 38, without obstructing the liquid communication between the port 38 and the suction lumen 36 proximal to the port 38. This allows the port 38 to be located very close to the cuff 12 which should provide for more thorough suctioning of secretions from the subglottic space above the cuff.

The proximal collar 26 may also block the part of the suction lumen 36 that is distal to the port 38, instead of merely laying in or on the port 38. Purposely occluding the suction lumen 36 in this manner makes the sealing plug 39 unnecessary, though it may still be used to ensure that the suction lumen 36 distal to the suction port 38 is completely sealed.

Figure 4:
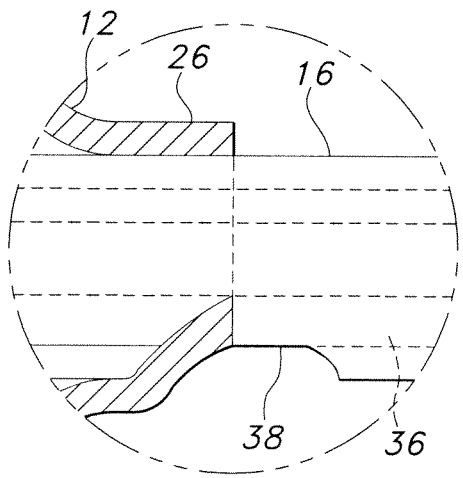
FIG. 4 is a close-up side view of the suction port of FIG. 3.

FIG. 4 is a close-up side view of the suction port at the circle 4 of FIG. 3. In this view, the proximal part of the suction lumen 36 is open just above the cuff 12 and communicates with the suction lumen port 38. The proximal collar 26 is attached to the cannula 16 in a manner that allows it to enter the port 38. It may block the distal part of the suction lumen 36. Since the collar 26 enters into the distal or lower portion of the open port 38, it affects only the part of the suction lumen 36 distal to the port 38 while still allowing liquid communication between the proximal portion of the suction lumen 36 with the port 38.

Figure 5:
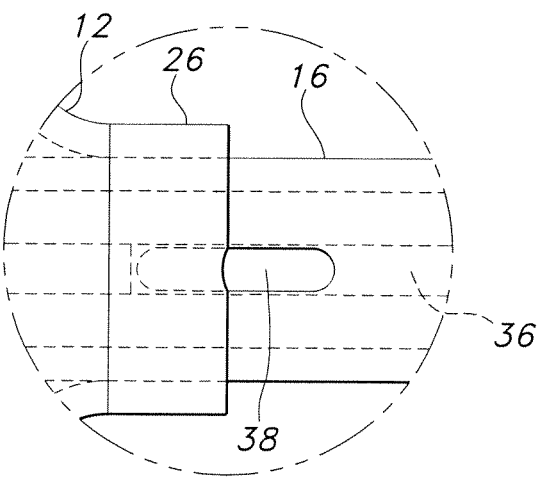
FIG. 5 is a frontal close-up view of the suction port according to this disclosure.

FIG. 5 shows a frontal close-up view of the suction lumen port 38, partially is covered by the collar 26. The proximal part of the suction lumen 36 is in liquid communication with the suction lumen port 38. Note, in FIGS. 2-5 the distal direction is to the left of the drawings. It should also be noted that although the port 38 shown in FIG. 5 is oval shaped, the depicted shape is not meant as a limitation. The port may be round, square or any other shape that is functional.

The tracheal tube of the embodiments shown in FIGS. 3-5 and described above allows for the suction lumen port to be placed in close proximity to the inflatable cuff. This allows for better, more thorough suctioning of secretions from the subglottic space. This also reduces the likelihood that the suction port will attach to the tracheal wall during the application of suction, and so reduces the chance of tracheal trauma.

The collar 26 is usually attached to the cannula 16 with an adhesive. A suitable adhesive is available from Dymax Corporation of Torrington, Conn. as item number 1163-M#F0024-FH076 though other suitable adhesives are available. This Dymax adhesive is an ultra-violet curable adhesive. Other methods of attaching the collars to the cannula may also be used. These include thermal bonding, solvent bonding, radio frequency and ultrasonic bonding and other means known to those skilled in the art.

In order to minimize leakage past the cuff and into the lungs, the disclosed tracheal tube desirably uses an improved cuff design. A tracheal tube using the cuffs taught in U.S. Pat. No. 6,526,977 or 6,802,317 results in much less leakage past the cuff into the lungs than conventional thick cuffs allow. The '977 and '317 cuffs are desirably made from a soft, pliable polymer such as polyurethane, polyethylene teraphihalate (PETP), low-density polyethylene (LDPE), polyvinyl chloride (PVC), polyurethane (PU) or polyolefin. The cuff should be very thin; with a thickness on the order of 25 microns or less, e.g. 20 microns, 15 microns, 10 microns or even as low as 5 microns in thickness, though at least 1 micron. The cuff should also desirably be a low pressure cuff operating at an inflation pressure of about 30 mmH$_2$O or less, such as 25 mmH$_2$O, 20 mmH$_2$O, 15 mmH$_2$O or less.

U.S. Pat. No. 6,802,317 describes a tracheal tube for obturating a patient's trachea as hermetically as possible, comprising: a cuffed balloon which blocks the trachea below a patient's glottis, an air tube, the cuffed balloon being attached to the air tube and being sized to be larger than a tracheal diameter when in a fully inflated state and being made of a soft, flexible foil material that forms at least one draped fold in the cuffed balloon when inflated in the patient's trachea, wherein the foil has a wall thickness below or equal to 0.01 mm and the at least one draped fold has a loop found at a dead end of the at least one draped fold, that loop having a small diameter which inhibits a free flow of secretions through the loop of the at least one draped fold.

U.S. Pat. No. 6,526,977 teaches a cuff for obturating a patient's trachea as hermetically as possible, comprising a cuffed balloon which blocks the trachea below a patient's glottis, an air tube, the cuffed balloon being attached to the air tube and being sized to be larger than a tracheal diameter when in a fully inflated state and being made of a sufficiently soft, flexible foil material that forms at least one draped fold in the cuffed balloon when fully inflated in the patient's trachea, wherein the at least one draped fold formed has a capillary size which arrests free flow of secretions across the balloon by virtue of capillary forces formed within the fold to prevent aspiration of the secretions and subsequent infections related to secretion aspiration.

Since the '977 and 317 cuffs inhibit or arrest the free flow of secretion past the cuff, the secretions build up above the cuff and discontinuous or intermittent suctioning may be used. Intermittent suctioning is safer for the tracheal wall since it reduces the chance that the suction lumen inlet will adhere to the wall and subject it to the force of suction.

At the discretion of the caregiver and particularly immediately prior to removal of the tracheal tube, the subglottic space within the patient's trachea may be suctioned through the suction lumen 36 via the port 38 through the wall 25 of the cannula 16. During this process, ventilation of the patient through the respiratory gas-conveying lumen 22 may of course continue unaffected.

Other arrangements are included in the spirit and scope of the disclosure. For example, the layout of the lumens within the cannula 16 may be altered, moreover, the suction lumen 36 may be formed in another wall or it may be a self contained lumen not embedded within any one of the walls of the cannula 16. In addition, as alluded to above, other lumens may be present in the cannula 16, such as rinse lumens to deliver fluid to loosen or dilute thick secretions prior to suctioning or lumens to deliver anesthesia or other medicaments. These additional lumens are not depicted though are understood by those skilled in the art.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

We claim:

1. A tracheal catheter comprising:
    a cannula having a respiratory lumen and a suction lumen and an inflatable cuff, the suction lumen terminating in a suction lumen port proximal to the inflatable cuff to allow suctioning of the subglottic space external to the cannula while simultaneously enabling ventilation through the respiratory lumen;
    said inflatable cuff having an upper collar that attaches to the cannula and overlays and blocks a portion of the suction lumen that is distal to the port.

2. The tracheal catheter of claim 1 wherein the upper collar is located at least partially in said suction lumen port, without obstructing the suction lumen proximal to said suction lumen port.

3. The tracheal catheter of claim 1 wherein the cuff is attached to said cannula with an adhesive.

4. The tracheal catheter of claim 3 wherein said adhesive is curable with ultra-violet light.

* * * * *